(12) United States Patent
Patel et al.

(10) Patent No.: US 10,888,514 B1
(45) Date of Patent: Jan. 12, 2021

(54) COSMETIC COMPOSITIONS

(71) Applicant: L'OREAL, Paris (FR)

(72) Inventors: Sonal J. Patel, Iselin, NJ (US); Balanda Atis, Green Brook, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/580,615

(22) Filed: Sep. 24, 2019

(51) Int. Cl.
| | |
|---|---|
| *A61K 8/00* | (2006.01) |
| *A61K 8/891* | (2006.01) |
| *A61K 8/92* | (2006.01) |
| *A61K 8/25* | (2006.01) |
| *A61K 8/26* | (2006.01) |
| *A61K 8/27* | (2006.01) |
| *A61K 8/58* | (2006.01) |
| *A61Q 1/06* | (2006.01) |
| *A61Q 1/10* | (2006.01) |
| *A61K 8/29* | (2006.01) |

(52) U.S. Cl.
CPC ............... *A61K 8/891* (2013.01); *A61K 8/25* (2013.01); *A61K 8/26* (2013.01); *A61K 8/27* (2013.01); *A61K 8/29* (2013.01); *A61K 8/585* (2013.01); *A61K 8/92* (2013.01); *A61Q 1/06* (2013.01); *A61Q 1/10* (2013.01); *A61K 2800/31* (2013.01); *A61K 2800/43* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 6,027,738 A | 2/2000 | Stepniewski et al. | |
| 6,103,250 A | 8/2000 | Brieva et al. | |
| 6,960,339 B1 | 11/2005 | Ferrari et al. | |
| RE39,218 E | 8/2006 | Mellul et al. | |
| 2005/0187128 A1 | 8/2005 | Guenaelle et al. | |
| 2006/0013790 A1 | 1/2006 | Shimizu | |
| 2007/0274939 A1 | 11/2007 | Guerra et al. | |
| 2011/0110991 A1* | 5/2011 | Garrison | A61K 8/26 424/401 |
| 2016/0166479 A1 | 6/2016 | Chiou et al. | |

FOREIGN PATENT DOCUMENTS

EP    1068856 A1    4/2003

OTHER PUBLICATIONS https://www.skinstore.com/dermable nd-flawless-creator-liquid-foundation-drops-30ml-various-shades/11527835.html, accessed Aug. 30, 2019, pp. 1-2
https://www.dermablend.com/poresaver-matte-makeup-primer/3606000525399.html, accessed Aug. 30, 2019, pp. 1-2.
Diezel, C., "How to Convert from Centistokes to Centipoise", (https://sciencing.com/convert-centistoke-centipoise-8279085.html (updated Mar. 13, 2018)(Year: 2018).
"Concealer SPF 20", Almay, MINTEL GNPD record ID 4284153, published Sep. 2016, p. 1-3.
"Lip Exilir SPF 15", Oriflame, MINTEL GNPD record ID 5683775, published on May 2018, p. 1-5.
"Powder Effect Mousse Foundation SPF 15", Cosmeticos Nature, MINTEL GNPD record ID 2789805, published on Nov. 2014, p. 1-4.
"Matte Ink Lip Color", Maybelline, MINTEL GNPD record ID 6576007, published on May 2019, p. 1-3.
"Matte Ink Liquid Lip Coior", Maybelline, MINTEL GNPD record ID 6510757, published on Apr. 2019, p. 1-3.
"Lip Wardrobe vol. II Collection", Tarte, MINTEL GNPD record ID 4816433, published on May 2017, p. 1-4.

* cited by examiner

*Primary Examiner* — Susan T Tran

(57) ABSTRACT

The present disclosure relates to anhydrous cosmetic composition comprising a silicone oil; a spherical powder; a pigment; silicone emulsifier; hydrophobic silica particles; and a silicone resin, wherein the cosmetic composition is essentially free of water.

2 Claims, No Drawings

COSMETIC COMPOSITIONS

FIELD OF THE DISCLOSURE

The present invention relates to cosmetic compositions and to the uses of such compositions, in particular in the cosmetic and/or dermatological fields.

BACKGROUND

In the field of cosmetic compositions, it is known to use soft-focus minerals or organic fillers that absorb sebum and perspiration, in order to achieve various benefits (for example, skin mattifying or smoothness).

However, the use of these materials are sometimes accompanied by a dry, rough feel and lack of comfort that is unacceptable for the user.

Silicone elastomers are also widely used as mattifying agents because also tend to provide a soft feel on the skin. However, they must be used at a relatively high content in order to have the mattifying effect, and these may create dry and coarse (i.e. cakey) texture.

Accordingly, there is still a need for cosmetic compositions that have mattifying effects on the skin, and which have good properties, in particular which are soft on application. Moreover, the inventors of the instant invention have recognized that a sensation of comfort during application and a silky skin feel after skin penetration are desired.

SUMMARY OF THE INVENTION

One aspect of the present invention pertains to a cosmetic composition
comprising:
  a silicone oil;
  a spherical powder;
  a pigment;
  silicone emulsifier;
  hydrophobic silica particles; and
  a silicone resin,
wherein the cosmetic composition is essentially free of water. In one or more embodiments, the cosmetic composition is anhydrous. In some embodiments, the silicone oil is present in a concentration by weight that is from about 40% to about 75%. In one or more embodiments, the silicone oil is selected from the group consisting of a polymerized siloxane, polydimethylsiloxane, cyclosiloxanes, and combinations thereof. In some embodiments, the spherical powder is present in a concentration by weight that is greater than 5%. In one or more embodiments, the spherical powder is selected from the group consisting of silica, silica-based composite oxides, aluminum oxide, titanium oxide, zinc oxide, silicone resins, acrylate-based polymers, polyurethane-based polymers, nylon-12, polyethylene and polystyrene, and combinations thereof. In some embodiments, the pigment is present in a concentration by weight that is from about 0.5 to about 20%. In one or more embodiments, the pigment is selected from the group consisting of organic pigments. In some embodiments, the pigment is selected from the group consisting of treated and untreated iron oxide, titanium dioxide and combinations thereof. In one or more embodiments, the silicone emulsifier is present in a concentration by weight that is from about 1 percent to about 5%. In some embodiments, the silicone emulsifier is selected from a group consisting of polyglyceryl silicone, dimethicone copolyol, and combinations thereof. In one or more embodiments, the hydrophobic silica particles are present in a concentration by weight that is from about 0.25 percent to about 5 percent. In some embodiments, the hydrophobic silica particles comprise silica silylate particles. In one or more embodiments, the silicon resin is present in a concentration by weight that is from about 0.25 percent to about 5 percent. In some embodiments, the silicon resin comprises a siloxysilicate resin.

Another aspect of the invention pertains to a cosmetic composition,
  comprising:
  about 40 to about 75% by weight of a silicone oil;
  more than about 5% by weight of a spherical powder;
  about 0.5 to about 20% by weight of a pigment;
  about 1 to about 5% by weight of silicone emulsifier;
  about 0.25 to about 5% by weight of hydrophobic silica particles; and
  about 0.25 to about 5% by weight of a silicone resin,
and wherein the cosmetic composition is essentially free of water.

In one or more embodiments, the composition comprises:
  about 40 to about 75% by weight of a silicone oil comprising dimethicone;
  more than about 5% by weight of a spherical powder comprising amorphous silica;
  about 0.5 to about 20% by weight of a pigment comprising iron oxide, titanium dioxide and combinations thereof;
  about 1 to about 5% by weight of silicone emulsifier comprising PEG-10 dimethicone;
  about 0.25 to about 5% by weight of hydrophobic silica particles comprising silica silylate; and
  about 0.25 to about 5% by weight of a silicone resin comprising trimethylsiloxysilicate,
  and wherein the cosmetic composition is anhydrous.

In some embodiments, the composition comprises:
  about 50 to about 60% by weight of a silicone oil comprising dimethicone;
  about 5 to about 15% by weight of a spherical powder comprising amorphous silica;
  about 5 to about 15% by weight of a pigment comprising iron oxide and titanium dioxide and combinations thereof;
  about 2 to about 5% by weight of silicone emulsifier comprising PEG-10 dimethicone;
  about 1 to about 3% by weight of hydrophobic silica particles comprising silica silylate; and
  about 0.5 to about 2% by weight of a silicone resin comprising trimethylsiloxysilicate.

DETAILED DESCRIPTION OF THE INVENTION

As used herein, the terms "comprises", "comprising," "having," and "including" are used in their open, non-limiting sense.

The terms "a," "an," and "the" are understood to encompass the plural as well as the singular. Thus, the term "a combination thereof" also relates to "combinations thereof." Throughout the disclosure, the term "a mixture thereof or combination thereof" is used, following a list of elements as shown in the following example where letters A-F represent the elements: "one or more elements selected from the group consisting of A, B, C, D, E, F, and a combination thereof." The term, "a combination thereof" does not require that the combination include all of A, B, C, D, E, and F (although all of A, B, C, D, E, and F may be included). Rather, it indicates that a combination of any two or more of A, B, C, D, E, and F can be included. In other words, it is equivalent to the phrase "one or more elements selected from the group consisting of A, B, C, D, E, F, and a combination of any two or more of A, B, C, D, E, and F."

The term "INCI" is an abbreviation of International Nomenclature of Cosmetic Ingredients, which is a system of names provided by the International Nomenclature Committee of the Personal Care Products Council to describe personal case ingredients.

The term "active weight" refers to the amount of a particular ingredient exclusive of any solvent, carrier, impurities and the like that may be supplied with particular ingredient.

The term "solid basis" or "solid content" means considering only components (e.g., in a composition) that are solid at room temperature and ignoring portions of the composition that are liquid, e.g., water and other volatile solvents.

The expression "one or more" means "at least one" and thus includes individual components as well as mixtures or combinations.

Other than in the operating examples, or where otherwise indicated, all numbers expressing quantities of ingredients and/or reaction conditions are to be understood as being modified in all instances by the term "about," meaning within +/−5% of the indicated number.

The term "anhydrous" as used herein means that there is less than about 2% by weight of water added to a composition, based on the total weight of the composition. Nonetheless, the compositions may include less than about 1 wt. %, less than about 0.5 wt. % less than about 0.1 wt. %, or none at all.

All percentages, parts and ratios herein are based upon the total weight of the compositions of the present invention, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material.

The term "copolymer" as used herein refers to polymers formed from at least two different types of monomers.

The term "pigment" as used herein means any colored and/or iridescent mineral or organic particles that are insoluble in the liquid hydrophilic phase, which are intended to color and/or add iridescence to the composition.

Accordingly, one aspect of the invention pertains to a cosmetic
   composition comprising:
   a silicone oil;
   a spherical powder;
   a pigment;
   silicone emulsifier;
   hydrophobic silica particles; and
   a silicone resin,
wherein the cosmetic composition is essentially free of water.

Such compositions have been found to provide smooth texture and are able to control oily skin throughout the day, as well as maintain a matte finish without feeling dry. They may be particularly suitable as foundations, although they may also be useful as other cosmetic compositions such as lipsticks, eye shadows, etc.

Silicone Oils

The term "silicone oil" means an oil comprising at least one silicon atom, and especially comprising Si—O groups. The silicone oil(s) may be volatile or non-volatile.

As used herein, by "oils" or "oil" it is meant compounds having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy) sulfonyl moieties. In certain embodiments, the oil does not include hydroxyl moieties.

In certain embodiments, the silicone oil that may be used in the present invention may be chosen from silicone oils with a flash point ranging from 40° C. to 150° C., preferably with a flash point of greater than 55° C. and less than or equal to 105° C., and preferentially ranging from 65° C. to 95° C. The flash point is measured in particular according to standard ISO 3679.

The term "volatile" refers to a compound that can evaporate on contact with the skin in less than one hour, at room temperature and atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa (10"3 to 300 mmHg), preferably ranging from 1.3 Pa to 13 000 Pa (0.01 to 100 mmHg) and preferentially ranging from 1.3 Pa to 1300 Pa (0.01 to 10 mmHg).

In certain embodiments, the volatile silicone oils that may be mentioned include cyclopolydimethylsiloxanes (INCI name: cyclomethicone), such as cyclopentasiloxane, cyclohexasiloxane, octylmethylcyclotetrasiloxane, decamethylcyclopentasiloxane, dodecamethylcyclohexasiloxane; linear silicones such as heptamethylhexyltrisiloxane, heptamethyloctyltrisiloxane, hexamethyldisiloxane, octamethyltrisiloxane, decamethyltetrasiloxane and dodecamethylpentasiloxane.

In certain embodiments, the silicone oil may be chosen from linear or cyclic silicone oils, such as linear or cyclic polydimethylsiloxanes (PDMSs) (INCI name: dimethicone), which are liquid at room temperature, especially cyclopolydimethylsiloxanes (cyclomethicones) such as cyclohexasiloxane; polydimethyl-siloxanes comprising alkyl, alkoxy or phenyl groups, which are pendent or at the end of a silicone chain, these groups containing from 2 to 24 carbon atoms, phenyl silicones, for instance phenyl trimethicones, phenyl dimethicones, phenyltrimethylsiloxydiphenyl-siloxanes, diphenyl dimethicones, diphenylmethyl-diphenyltrisiloxanes or 2-phenylethyl trimethylsiloxy silicates, and polymethylphenylsiloxanes, combinations thereof.

In one or more embodiments, the silicone oil may have a viscosity ranging from about 0.5 cSt to about 350 cSt.

The concentration of silicone oils may be present in a composition in accordance with the invention in a content ranging from about 40%, 45%, 50%, 55%, or 60% to about 60%, 65%, 70%, or 75% by weight, including all ranges and subranges there between, all weights being based on the total weight of the composition.

Spherical Powder

The composition according to the present invention comprises a spherical powder. Examples of spherical powders which are suitable for use include powders of silica, silica-based composite oxides, aluminum oxide, titanium oxide, zinc oxide, silicone resins, acrylate-based polymers, polyurethane-based polymers, nylon-12, polyethylene and polystyrene. Porous and non-porous spherical powders may also be used in combination. Other representative stabilizing spherical cosmetic powders may be selected, in some embodiments, from polymer based microspheres, in particular, plastic microspheres, that include, but are not limited to, methyl methacrylate crosspolymer, HDI/trimethyl hexyllactone crosspolymer, Ethylene/Methacrylate Copolymer, polylactic acid, polymethylsilsesquioxane, polymethyl methylacrlyate, methylmethacrylate crosspolymer, ethylene, acrylic acid copyolymer, aluminimum chlorohudrate, polyethylene, acrylates/ethylhexyl acrylate crosspolymer (and) sodiumpolyacrylate, polylactic acid (and) polyglyceryl-5 laurate, and combinations thereof.

The concentration of spherical powders may be present in a composition in accordance with the invention in a content ranging from greater than about 5% or about 5%, 6%, 7%, 8%, 9%, or 10% to about 7%, 8%, 9%, 10%, 11%, 12%, 13%, 14%, or 15% by weight, including all ranges and subranges there between, all weights being based on the total weight of the composition.

Pigments

According to one or more embodiments of the present invention, compositions may further comprise at least one pigment, which may include inorganic pigments, organic pigments or lakes. They may be surface-treated.

The pigments can also be inorganic; inorganic pigments include iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide (white), zinc oxide and mixtures thereof. Also useful are transparent metal oxide-coated silica beads. Metal oxides, particularly iron and titanium oxides, are the most common color components of makeups, particularly foundations and concealers. However, one of the primary advantages of the present system is that it permits the creation of a highly effective concealer without the presence of large amounts of metal oxide pigments, which render the makeup heavier and more opaque, and thus leave the skin looking somewhat unnatural.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

While in certain embodiments, compositions of the present invention include pigments in a content ranging from about 0.5%, 1%, 3%, or 5% to about 10%, 15%, or 20% by weight, including all ranges and subranges there between, all weights being based on the total weight of the composition.

Silicone Emulsifiers

In certain embodiments, useful emulsifiers for the composition of the present invention are those with an HLB (hydrophilic-lipophilic balance) no greater than 7. Although any cosmetically acceptable emulsifier with an HLB no greater than 7 can be used in the compositions, excellent results can be obtained using silicone based emulsifiers (sometimes referred to herein as "silicone emulsifier"). Examples of some useful silicone emulsifiers are: (1) dimethicone and PEG/PPG-18/18 dimethicone (e.g., X-22-6711D from Shin-Etsu); (2) dimethicone and dimethicone crosspolymer (e.g., Dow Corning 9041 Silicone Elastomer Blend); (3) dimethicone and dimethicone/PEG-10/15 crosspolymer (KSG-210 from Shin-Etsu); and (4) dimethicone and dimethicone/polyglycerin-3 crosspolymer (KSG 710 from Shin-Etsu).

In certain embodiments, the silicone emulsifier that may be used in the present invention may be chosen from polyether substituted linear or branched polysiloxane copolymers. One particular co-emulsifier is PEG-10 dimethicone available under the tradename of ES-5612 from Dow Corning Corporation (Midland, Mich.), or KF-6017 from Shin-Etsu (Akron, Ohio). Another preferred co-emulsifier is dimethicone (and) PEG/PPG-18/18 dimethicone available under the tradename of ES-5226 DM from Dow Corning Corporation (Midland, Mich.) Other suitable co-emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio).

The concentration of silicone emulsifier may be present in a composition in accordance with the invention in a content ranging from about 1%, 2%, or 3% to about 3%, 4%, or 5% by weight, including all ranges and subranges there between, all weights being based on the total weight of the composition.

Hydrophobic Silica Particles

The composition according to the present invention comprises hydrophobic silica particles.

The hydrophobic silica may be fumed (i.e., may be a "fumed silica"). The fumed silica may be obtained by modifying the surface of the silica via a chemical reaction that generates a reduction in the number of silanol groups, these groups possibly being substituted especially with hydrophobic groups.

The fumed silica is also known as pyrogenic silica, it is produced in a flame and generally consists of microscopic droplets of amorphous silica fused into branched, chainlike, three-dimensional secondary particles which then agglomerated into tertiary particles. The resulting powder has an extremely low bulk density and high surface area.

The hydrophobic groups may be:
a. trimethylsiloxyl groups, which may be obtained by modifying the surface of the silica via the presence of hexamethyldisilazane. Silicas thus treated are known as "Silica silylate" according to the CTFA (8th edition, 2000). They are sold, for example, under the references VM-2270 AEROGEL by the company Dow Corning.

b. dimethylsilyloxyl or polydimethylsiloxane groups, which are especially obtained by treating fumed silica in the presence of polydimethylsiloxane or dimethyldichlorosilane. Silicas thus treated are known as "Silica Dimethyl Silylate" according to the CTFA (8th Edition, 2000). They are sold, for example, under the references AEROSIL R972 and AEROSIL R974 by the company Degussa, and CAB-O-SIL TS-610 and CAB-O-SIL TS-720 by the company Cabot.

In general, the hydrophobic silica particles are present in an amount that is sufficient to adjust the hardness of the compositions according to the invention to the required value.

In certain embodiments, the hydrophobic silica particles may be fumed.

In one embodiment, the hydrophobic fumed silica particles are in the form of a white, free flowing powder. The particles are completely hydrophobic providing a vehicle for thickening oil phase materials, reducing the volatility of many volatile fluids and the absorption of may lipophilic materials including sebum.

According to certain embodiments of the invention, the hydrophobic fumed silica particles have a porosity greater than 90%, white, free-flowing, powder having bulk density of 40-100 kg/m$_3$, average particle size 5-15 microns, surface area 600-800 m$_2$/g.

An example of suitable hydrophobic fumed silica particles is those from Dow corning under the trade name VM-2270 AEROGEL.

The concentration of hydrophobic silica particles may be present in a composition in accordance with the invention in a content ranging from about 0.25%, 0.5%, 1 or 1.5% to about 2%, 2.5%, or 3% by weight, including all ranges and subranges there between, all weights being based on the total weight of the composition.

Silicone Resin

The cosmetic compositions of the present invention comprise at least one silicone resin such as described for example, in U.S. Pat. Nos. 5,505,937, 5,911,974, 5,965,112, 5,985,298, 6,074,654, 6,780,422, 6,908,621, the disclosures of which are hereby incorporated by references.

According to this invention, the cosmetic compositions may contain siloxysilicate resins. One non-limiting example of a siloxysilicate in accordance with the present invention is trimethylsiloxysilicate, which may be represented by the following formula:

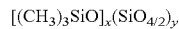

wherein x and y may, for example, range from 50 to 80. Such siloxysilicates are commercially available from General Electric, Dow Corning, Wacker, Milliken, Siltech, Grant Industries, Momentive and Shin-Etsu Silicones under the tradename Resin MQ®.

According to another embodiment of this invention, the compositions may contain silsesquioxane resins, including comprise at least one polypropyl silsesquioxane film forming resin.

Silsesquioxane resins are a specific form of silicone resin. Silicone resin nomenclature is known in the art as "MDTQ" nomenclature, whereby a silicone resin is described according to the various monomeric siloxane units which make up the polymer. Each letter of "MDTQ" denotes a different type of unit. When the film forming resin is made up predominantly of tri-functional units (or T units), it is generally called a silsesquioxane resin, which is described, for example in US 2006/0292096, herein incorporated by reference.

Examples of silsesquioxane resins that may be used in the present invention are alkyl silsesquioxane resins that are silsesquioxane homopolymers and/or copolymers having an average siloxane unit of the general formula $R^1_n SiO_{(4-n)/2}$, wherein each R1 is a propyl group, wherein more than 80 mole % of R1 represent a C3-C10 alkyl group, n is a value of from 1.0 to 1.4, and more than 60 mole % of the copolymer comprises $R^1SiO_{3/2}$ units. As each R1 is a propyl group these polymers are called polypropylsilsesquioxane resins or "t-propyl" silsesquioxane resins. These resins and methods of making them are described, for example in U.S. Pat. No. 8,586,013, 2012/0301415, 2007/0093619, and 2006/0292096, all of which are herein incorporated by reference.

A non-limiting example of a polypropylsilsesquioxane resin suitable for use in the present invention is commercially available from Dow Corning as Dow Corning 670 Fluid or Dow Corning 680 Fluid. These Dow Corning resins have a general formula of RnSiO(4–n)/2 wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $R^1SiO_{3/2}$ units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5000 to about 30,000 and a Tg from about −5° C. to about 5° C.

Another embodiment of this invention, exemplifies the composition containing at least one siloxysilicate resin, at least one silsesquioxane resin and/or mixture thereof.

The concentration of silicone resin may be present in a composition in accordance with the invention in a content ranging from about 0.25%, 0.5%, 1 or 1.5% to about 2%, 2.5%, or 3% by weight, including all ranges and subranges there between, all weights being based on the total weight of the composition.

Additional Ingredients

The composition of the present invention is substantially free of water.

The compositions may also benefit from the incorporation of one or more plate-like, non-spherical powders that confer some luster, but not an overt shine.

Examples of such powders include, but are not limited to, bismuth oxychloride, boron nitride, barium sulfate, mica, sericite, muscovite, synthetic mica, titanium oxide coated mica, titanium oxide coated bismuth oxychloride, titanium oxide coated talc, platelet iron oxides, metal powders such as aluminum, lauroyl lysine and platelet talc, to the extent these materials.

These powders, when used, are essentially present as fillers, and therefore may make up the bulk of the remainder of the product outside the essential and preferred components named above, and therefore the amount may be any amount needed to make up the remainder of the composition According to preferred embodiments of the present invention, the compositions of the present invention further may include wax. As used herein, "wax" is intended to mean a lipophilic fatty compound that is solid at room temperature (about 25° C.) and atmospheric pressure (760 mm Hg, i.e., 105 Pa), which undergoes a reversible solid/liquid change of state and which has a melting point of greater than 30° C., and in some embodiments, greater than about 55° C. up to about 120° C. or even as high as about 200° C.

The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

The cosmetic composition of the present invention may further include various additives desirably used in cosmetic or dermatological compositions. For example, fragrances, pearlescent agents, colorants, particulates, thickeners, dispersants, anti-oxidants, pH adjusters, preservatives, neutralizing agents, fragrances, fillers, co-solvents, plasticizers, cosmetic and dermatological active agents such as emollients, moisturizers, vitamins, UV filters, and sunscreens, and combinations thereof can be added. A non-exhaustive listing of such ingredients can be found in the CTFA *International Cosmetic Ingredient Dictionary and Handbook*, Fourteenth Edition (2012), contents of which are incorporated herein by reference in its entirety.

One skilled in the art will take care to select the optional additional additives and/or the amount thereof such that the advantageous properties of the mascara compositions according to the present invention are not, or are not substantially, adversely affected by the envisaged addition.

These substances may be selected variously by one skilled in the art to prepare a composition which has the desired properties, for example, consistency or texture.

Examples

Several formulations were prepared according to Table 1 below.

TABLE 1

| INCI US | Ex. 1 (Comp) | Ex. 2 (Comp) | Ex. 3 (Comp) | Ex. 4 (Inv) |
|---|---|---|---|---|
| DIMETHICONE CROSSPOLYMER | 3 | 5.25 | 3.6 | 3.6 |
| ISODODECANE | 19 | 7 | 12 | 12 |
| ISOHEMDECANE | | 31.94 | | |
| PEG-10 DIMETHICONE | 3.5 | 3.5 | 3.5 | 3.5 |
| SILICA SILYLATE | 1.25 | 1.25 | 1.25 | 1.25 |
| SYNTHETIC FLUORPHLOGOPITE | | 1.13 | 1.13 | 1.13 |
| TRIMETHYLSILOXYSILICATE | | | | 1 |
| DIMETHICONE | 54.06 | 29.75 | 58.34 | 57.34 |
| SILICA | 9 | 10 | 10 | 10 |
| PIGMENT (IRON OXIDES, TITANIUM DIOXIDE) | 10.19 | 10.18 | 10.18 | 10.18 |

TABLE 2

| Formula | Description of Stability |
|---|---|
| Ex. 1 (Comp.) | Separation; big layer of solvent on oil on top surface |
| Ex. 2 (Comp.) | Separation; some layer of solvent |
| Ex. 3 (Comp.) | Slight separation |
| Ex. 4 (Inv.) | No Separation |

As seen from Table 2, only the inventive formula was stable and featured no separation.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. accordingly, the description is not intended to limit the invention to the form disclosed herein. Also, it is intended to the appended claims to construed to include alternative embodiments.

What is claimed:

1. A cosmetic composition, comprising:
   about 40 to about 75% by weight of a silicone oil comprising dimethicone;
   more than about 6% by weight of a spherical powder comprising amorphous silica;
   about 0.5 to about 20% by weight of a pigment comprising iron oxide, titanium dioxide and combinations thereof;
   about 1 to about 5% by weight of silicone emulsifier comprising PEG-10 dimethicone;
   about 0.25 to about 5% by weight of hydrophobic silica particles comprising silica silylate; and
   about 0.25 to about 5% by weight of a silicone resin comprising trimethylsiloxysilicate,
   wherein the cosmetic composition is anhydrous.

2. The cosmetic composition of claim 1, wherein the composition comprises:
   about 50 to about 60% by weight of a silicone oil comprising dimethicone;
   about 6 to about 15% by weight of a spherical powder comprising amorphous silica;
   about 5 to about 15% by weight of a pigment comprising iron oxide and titanium dioxide and combinations thereof;
   about 2 to about 5% by weight of silicone emulsifier comprising PEG-10 dimethicone;
   about 1 to about 3% by weight of hydrophobic silica particles comprising silica silylate; and
   about 0.5 to about 2% by weight of a silicone resin comprising trimethylsiloxysilicate.

* * * * *